(12) United States Patent
Dupont

(10) Patent No.: US 6,383,522 B1
(45) Date of Patent: May 7, 2002

(54) TOXICITY REDUCED COMPOSITION CONTAINING AN ANTI-NEOPLASTIC AGENT AND A SHARK CARTILAGE EXTRACT

(75) Inventor: Eric Dupont, Saint-Nicolas (CA)

(73) Assignee: Les Laboratoires Aeterna, Inc., Québec (CA)

( * ) Notice: Subject to any disclaimer, the term of this patent is extended or adjusted under 35 U.S.C. 154(b) by 0 days.

(21) Appl. No.: 09/393,037

(22) Filed: Sep. 9, 1999

Related U.S. Application Data

(63) Continuation of application No. PCT/CA98/00202, filed on Mar. 11, 1998.

(30) Foreign Application Priority Data

Mar. 11, 1997 (CA) ............................................. 2199694

(51) Int. Cl.$^7$ ............................................. A61K 35/32
(52) U.S. Cl. ......................................................... 424/548
(58) Field of Search ......................................... 424/548

(56) References Cited

U.S. PATENT DOCUMENTS

| | | | |
|---|---|---|---|
| 3,478,146 A | 11/1969 | Balassa | 424/548 |
| RE28,093 E | 7/1974 | Balassa | 424/548 |
| 3,966,908 A | 6/1976 | Balassa | 424/548 |
| 4,042,457 A | 8/1977 | Kuettner et al. | 424/548 |
| 4,212,857 A | 7/1980 | Balassa et al. | 424/548 |
| 4,243,582 A | 1/1981 | Spilburg et al. | 530/395 |
| 4,350,682 A | 9/1982 | Balassa | 424/64 |
| 4,356,261 A | 10/1982 | Kuettner | 435/70.2 |
| 4,444,752 A | 4/1984 | Prudden | 424/548 |
| 4,456,589 A | 6/1984 | Holman et al. | 424/548 |
| 4,469,676 A | 9/1984 | Hecmati | 424/548 |
| 4,473,551 A | 9/1984 | Schinitsky | 424/548 |
| 4,656,137 A | 4/1987 | Balassa | 435/267 |
| 4,746,729 A | 5/1988 | Kuettner et al. | 530/353 |
| 4,749,522 A | 6/1988 | Kamarei | 554/8 |
| 4,822,607 A | 4/1989 | Balassa et al. | 424/548 |
| 5,075,112 A | 12/1991 | Lane | 42/434 |
| 5,096,892 A | 3/1992 | Folkman et al. | 514/56 |
| 5,135,919 A | 8/1992 | Folkman et al. | 514/56 |
| 5,583,153 A | 12/1996 | Brahn | 514/499 |
| 5,618,925 A | 4/1997 | Dupont et al. | 530/400 |
| 5,843,920 A | 12/1998 | Weisz | 514/58 |
| 5,985,839 A | 11/1999 | Dupont et al. | 514/21 |
| 6,025,334 A | 2/2000 | Dupont et al. | 512/21 |
| 6,028,118 A | 2/2000 | Dupont et al. | 514/863 |
| 6,168,807 B1 | 1/2001 | Dupont et al. | 424/548 |

FOREIGN PATENT DOCUMENTS

| | | | |
|---|---|---|---|
| JP | 45-001444 | 1/1970 | |
| JP | 59-039828 | 3/1984 | |
| JP | 60-178820 | 9/1985 | |
| WO | 9309766 | 5/1993 | |
| WO | 9412510 | 6/1994 | |
| WO | 9503036 | 2/1995 | |
| WO | 95/32722 | 12/1995 | A61K/35/60 |
| WO | 96/23512 | 8/1996 | A61K/35/60 |
| WO | 9716197 | 5/1997 | |

OTHER PUBLICATIONS

Horsman et al., Acta Oncologica (Stockholm) 37(5): 441–445 (1998). Abstract.*
Miller et al., Journal of Clinical Oncology 16(11): 3649–3655 (Nov. 1998). Abstract.*
Blood, Christine H. et al., "Tumor interactions with the vasculature: angiogenesis and tumor metastasis", *Biochemica et Biophysica Acta*, 1032: 89–118 (1990).
Brem, Steven, "Angiogenesis and Cancer Control: From Concept to Therapeutic Trial," *JMCC* 6(5): 436–458 (1999).
Davis–Smyth, Terri et al., "The second immunoglobulinlike domain of the VEGF tyrosine kinase receptor Flt–1 determines ligand binding and may initiate a signal transduction cascade," *The EMBO Journal* 15:18, 4919–4927 (1996).
Dupont, Eric et al., "Antiangiogenic Properties of a Novel Shark Cartilage Extract: Potential Role in the Treatment of Psoriasis," *Journal of Cutaneous Medicine and Surgery*, 2:3, 146–152 (1998).
Dvorak, H. F. et al., "Vascular Permeability Factor/Vascular Endothelial Growth Factor and the Significance of Micovascular Hyperpermeability in Angiogenesis," p. 98–132.
Fan, Tai–Ping D., "Controlling the vasculature: angiogenesis, anti–angiogensis and vascular targeting of gene therapy," *Angiogenesis Review*, 16, 57–66 (Feb. 1995).
Griffioen, Arjan W. et al., "Angiogenesis: Potentials for Pharmacologic Intervention in the Treatment of Cancer, Cardiovascular Diseases, and Chronic Inflammation," *Pharmacological Reviews*, 52:2, 237–268 (2000).
Hanahan, Douglas et al., "Patterns and Emerging Mechanisms of the Angiogenic Switch during Tumorigenesis," *Cell*, 86: 353–364 (Aug. 1996).
Jackson, Jeffrey R. et al., "The codependence of angiogenesis and chronic inflammation," *FASEB J*. 11, 457–465 (1997).
Kerr, Janet S. et al., "Novel Small Molecules αv Integrin Antagonists: Comparitive Anti–Cancer Efficacy with Known Agiogenesis Inhibitors," *Anticancer Research*, 19:959–968 (1999).
Passaniti, Antonio et al., "Methods in Laboratory Investigation: A Simple, Quantitative Method for Assessing Angiogenesis and Antiangiogenic Agents Using Reconstituted Basement Membrane, Heparin, and Fibroplast Growth Factor," *Laboratory Investigation*, 67:4, 519–528 (1992).

(List continued on next page.)

Primary Examiner—Jean C. Witz
(74) Attorney, Agent, or Firm—Akin, Gump, Strauss, Hauer & Feld, L.L.P.

(57) ABSTRACT

This invention described a novel use for cartilage extract, namely a shark cartilage extract, in a combined anti-tumor therapy. The cartilage extract is used in combination with anti-neoplastics. The combined therapy provides for a higher anti-tumor efficacy with no concomitant increase, even better with a decrease, of toxic side effects.

16 Claims, 3 Drawing Sheets

OTHER PUBLICATIONS

Pluda, James M., "Tumor–Associated Angiogenesis: Mechanisms, Clinical Implications, and Therapeutic Strategies," *Seminars in Oncology*, 24:2, 202–218 (Apr. 1997).

Weber, G., "Biochemical Strategy of Cancer Cells and the Design of Chemotherpy: G. H. A. Clowes Memorial Lecture," *Cancer Research*, 43: 3466–3492 (Aug. 1983).

Raju, KS et al., "Characterization of a chemoattractant for endothelium induced by angiogenesis effectors," *Cancer Res.*, 44(4): 1579–84 (Apr. 1984).

Rak, J. et al., "Treating cancer by inhibiting angiogenesis: new hopes and potential pitfalls," *Cancer and Metastasis Reviews* 15:231–236 (1996).

Sauder, Daniel N. et al., "Angiogenesis in Dermatology," *Curr Prob Dermacol*, 1–10 (May/Jun. 2001).

Siemeister, Gerhard et al., "Two Independent Mechanisms Essential for Tumor angiogenesis: Inhibition of Human Melanoma Xenograft Growth by Interfering with either the Vascular Endothelial Growth Factor Receptor Pathway or the Tie–2 Pathway," *Cancer Research* 59, 3185–3191 (Jul. 1, 1999).

Takano, Shingo et al., "Concentration of Vascular Endothelial Growth Factor in the Serum and Tumor Tissue of Brain Tumor Patients," *Cancer Research* 56, 2185–2190 (May 1996).

Laue, Thomas M. et al., *Methods in Enzymology*, 1990, 182:566–587.

Auerbach, W. et al., 1999, *Pharmac. Ther.* 1994; 63:265–311.

Bischoff, J., *Trend Cell Biol.*, 1995, 5:69–74.

Brooks, P.C., *Cancer Metastasis Rev.*, 1996, 15:187–194.

Brooks, P.C., *Eur. J. Cancer*, 1996, 32A:2423–9.

Bussolino, F. et al., *Eur. J. Cancer*, 1996, 32A:2401–12.

Ferrara, N., *Nature*, 1995, 376–467.

Ferrara, N. et al., *Endocrine Rev.*, 1997, 18:4–25.

Form, D. et al., *J. Cell Physiol.*, 1992, 152:196–205.

Hamada, J. et al. *Br. J. Cancer*, 1992, 66:349–354.

Hanson et al., *J. Bone & Min. Res.*, 1992, 7:1251–1258.

Ingber, *Sem. Cancer Biol.*, 1992, 3:57–63.

Jaffe et al., *J. of Clin. Invest.*, 1973, 52:2745–2756.

Klagsrun, M. et al., *Annu. Rev. Physiol.*, 1991, 53:217–32.

Klein, S. et al., *Mol. Biol. Cell.*, 1993, 4:973–82.

Klein, S. et al., *J. Biol. Chem.*, 1996, 271:22583–90.

Knight et al., *FEBS Let.*, 1992, 296, 263–266.

Knighton, D.R. et al., *Science*, 1983, 221:1283–85.

Koch, A. E. et al., *Nature*, 1995, 376:517–19.

Laemmli, U.K., *Nature*, 1970, 227:680.

Mazure, N. M. et al., *Cancer Res.*, 1996, 56:3436–40.

Mignatti, P. et al., *J. Cell Biol.*, 1994, 113:1193–201.

Moses, M. A. et al., *Int. Rev. Cytol.*, 1995, 161:1–48.

Pepper, M. S. et al., *J. Cell Physiol.*, 1992, 152:196–205.

Pepper, M. S. et al.,*Biochem. Biophys. Res. Commun.*, 1992, 189:824–31.

Polverini, P. J., *Eur. J. Cancer*, 1996, 32A:2430–7.

Proost, P. et al., *Int. J. Clin. Lab. Res.*, 1996, 26:211–23.

Rak, J. et al., *Eur. J. Cancer*, 1996, 32A:2438–50.

Rak, J. E. et al., *J. Cell Physiol.,,* 1994, 159:245–55.

Rosen and Woodhead, *Medical Hypotheses*, 1980, 6:441–446.

Sandner, P. et al., *Kidney Int.*, 1997, 51:448–53.

Schwartz, S. M. et al., *J. Cardiovasc. Pharmacol.*, 1993, 21 Suppl. 1:S31–S49.

Schweigerer, L. et al., *Nature*, 1987, 325:258–9.

Welgus et al., *J. Biol. Chem.*, 1979, 256:9511–9516.

Wilkin, J. K., *Arch. Dermatol.*, 1994, vol. 130, 359–362.

Oikawa, T., H. Ashino–Fuse, M. Shimamura, U. Koide and T. Kwaguchi, "A novel angiogenic inhibitor derived from Japanese shark cartilage (I). Extraction and estimation of inhibitory activities toward tumor and embryonic angiogenesis," *Cancer Letters*, 51 (1990) 181–186.

Moses, Marsha A. and Robert Langer, "Inhibitors of Angiogenesis," *Biotech* 1991;9:, pp. 630–634.

Folkman, Judah and Michael Klagsbrun, "Angiogenic Factors," *Science*, vol. 235, pp. 442–446.

Luer, C. A., "Inhibitors of Angiogenesis from Shark Cartilage," Fed. Proc. 45(4):949.

Suzuki, Fujio, Masaharu Takigawa, Yugi Hiraki, Yukio Kato, Keisuke Fukuo, Tsuyoshi Shiio and Yasumi Yugari, "Cartilage–derived Antitumor Factor (CATF): A High Molecular Weight Fraction Cartilage Extract Inhibits Solid Tumor Growth," *Journal of Bone and Mineral Metabolism*, 1984 vol. 2 No. 3, pp. 53–57.

Langer, Robert, Henry Brem, Kenneth Falterman, Michael Klein, Judah Folkman, "Isolation of a Cartilage Factor That Inhibits Tumor Neovascularization," *Science*, vol. 193, pp. 70–72.

Sorgente, Nino, Ph.D., Klaus E. Kuettner, Ph.D., Lawrence W. Soble, M. S., and Reuben Eisenstein, M. D., "The Resistance of Certain Tissues to Invasion," *Laboratory Investigation*, vol. 32, No. 2, 1975, pp. 217–222.

Brem, Henry and Judah Folkman, "Inhibition of Tumor Angiogenesis Mediated by Cartilage," *The Journal of Experimental Medicine*, vol. 141, 1975, pp. 427–439.

Kuettner, Klaus E., Lawrence Soble, Richard L. Croxen, Barbara Marczynska, Judith Hiti, and Elvin Harper, "Tumor Cell Collagenase and Its Inhibition by a Cartilage–Derived Protease Inhibitor," *Science*, ol. 196, pp. 653–654.

Weingarten, Martin and Feder (1985), "Synthetic Substrates of Vertabrate Collagenase," *Biochemistry* 24, 6730–6734.

Sadove, Alan Michael, MD, MS and Klaus E. Kuettner, Ph.D., "Inhibition of Mammary Carcinoma Invasiveness with Cartilage–Derived Inhibitor," *Orthopaedic Surgery*, pp. 499–501.

Paull, Bendicht U., Vincent A. Memoll, and Klaus E. Kuettner, "Regulation of Tumor Invasion by Cartilage–Derived Anti–Invasion Factor in Vitro," *JNCI*, vol. 67, No. 1, Jul. 1981, pp. 65–73.

Morales, T. I., K. E. Kuettner, D. S. Howell and J. F. Woessner, "Characterization of the Metalloproteinase Inhibitor Produced by Bovine Articular Chondrocyte Cultures," *Biochimic et Biophysica Acta*, 760 (1983), pp. 221–229.

Moses, Marsha A., Judith Sudhalter and Robert Langer, "Indentification of an Inhibitor of Neovascularization from Cartilage," *Science*, vol. 248, pp. 1408–1410.

Moses, Marsha A. and Robert Langer, "A Metalloproteinase Inhibitor as an Inhibitor of Neovascularization," *Journal of Cellular Biochemistry*, vol. 47, 1991, pp. 230–235.

Moses, M. A., "A Cartilage–Derived Inhibitor of Neovascularization and Metalloprotteinases," *Clinical and Experimental Rheumatology* 11 *(Supp. 8)*, 1993, pp. S67–S69.

Moses, Marsha A. and Robert Langer, "Metalloproteinase Inhibition as a Mechanism for the Inhibition of Angiogenesis," *Angiogensis: Key Principles–Science–Technology–Medicine*, 1992, pp. 146–151.

McGuire, Timothy R., Peter W. Kazakoff, Eric B. Hoie, and Margery A. Fienhold, "Antiproliferative Activity of Shark Cartilage With and Without Tumor Necrosis Factor–α in Human Umbilical Vein Endothelium, " *Pharmacotherapy*, 1996;16(2), p. 237.

Lee, Anne and Robert Langer, "Shark Cartilage Contains Inhibitors of Tumor Angiogenesis," *Science*, vol. 221, pp. 1186–1187.

Medina (1976), "Mammary Tumorigenesis in Chemical Carcinogen–Treated Mice. VI. Tumor–Producing Capabilities of Mammary Dysplasias in BALB/cCrgl Mice," *J. Natl. Cancer Inst.* vol. 57, No. 5, pp. 1185–1189.

Davis, Paul F., Yi He, Richard H. Furneaux, Peter S. Johnston, Beate M. Ruger and George C. Slim, "Inhibition of Angiogenesis by Oral Ingestion of Powdered Shark Cartilage in a Rat Model," *Microvascular Research*, vol. 54 (1997), pp. 178–182.

Mathews, James, "Media Feeds Frenzy Over Shark Cartilage As Cancer Treatment," *Journal of the National Cancer Institute*, vol. 85, No. 15, Aug. 4, 1993, p. 1190.

Scott et al., "Selective Demineralization of Hard Tissues in Organic Solvents: Retention or Extraction of Proteoglycan?", J. Microsc., 134(3), pp. 291–297.

Pavia et al., "Introduction to Organic Laboratory Techniques a Contemporary Approach," $2^{nd}$ Ed., Saunders College Publishing, Philadelphia, pp. 500–501.

Burdick & Jackson, "Highly Purity Solvent Guide," $2^{nd}$ Ed., Burdick & Jackson Laboratories, Inc., pp. 128–137.

Sheu, Fu, Tsai and Chung, "Effect of U–995, a Potent Shark Cartilage–Derived Angiogenesis Inhibitor, on Anti–Angiogenesis and Anti–Tumor Activities," Abtucabcer Researcg 18L 4435–4442 (1998).

Arnett, F. C. et al., (1988), Arthritis & Rheumatism, 31(3):315–324.

Chabot–Fletcher, M. et al. (1994), "Interleukin–8 Production is Regulated by Protein Kinase C in Human Keratinocytes," *The Journal of Investigative Dermatology*, 103(4):509–515.

Elias, P. M. (1993), "Epidermal Lipids, Barrier Function, and Desquamation," *J. Invest. Dermatol.* 80:044s–049s.

Grove, G. L. (1994), "Age–Related Differences in Healing of Superfical Skin Wounds in Humans" in *The effects of aging in oral mucosa and Skin.* ed. Squier & Hill CRC Press, pp. 127–127.

Matsui, M. S. et al. (1992), "Protein Kinase C in Normal Human Epidermal Keratinocytes During Proliferation and Calcium–Induced Differenciation, " *J. Invest. Dermatol.* 99: 565–571.

Medina, D. and K. B. DeOME (1969), "Response of Hyperplastic Aveolar Nodule Outgrowth–Line D1 to Mammary Tumor Virus, Nodule–Inducing Virus, and Prolonged . . ." *J. Natl. Cancer Inst.* 42: 303–310.

Nickoloff, B. J. et al. (1994), "Aberrant Production of Interleukin–8 and Thrombospondin–1 Psoriastic Keratinocytes Mediates Angiogenesis," *Am. J. Pathology* 144(4): 820–828.

Oresajo, C. et al. (1987), "Eye Area Problems Puffiness, Bags, Dark Circles and Crowsfeet," *Cosmetics and Toiletries* 102:29–34.

Pinnagoda (1990), "Guidelines for transepidermal water loss (TEWL) measurement," *Contact Dermatitis* 22: 164–178.

Ritchie, Boyle, McInnes, Jasani, Dalakos, Grieveson and Buchanan (1968), "Clinical Studies with an Articular Index for the Assessment of Joint Tenderness in Patients with Rheumatoid Arthritis," *Quarterly Journal of Medicine, New Series XXXVII*, No. 147, pp. 147, pp. 393–407.

* cited by examiner

TOXICITY REDUCED COMPOSITION CONTAINING AN ANTI-NEOPLASTIC AGENT AND A SHARK CARTILAGE EXTRACT

This application is a continuation of copending International Patent Application No. PCT/CA98/00202, filed Mar. 11, 1998, and which claims priority from Canadian Patent Application No. 2,199,694, filed Mar. 11, 1997.

Anti-tumor therapies comprising a combination of a cartilage extract and an anti-neoplastic agent providing high efficacy and low toxic side effects.

FIELD OF THE INVENTION

This invention relates to anti-tumor therapies which comprises anti-neoplastic agents and a cartilage extract having anti-tumor activity.

BACKGROUND OF THE INVENTION

Present assignee already described the biological activities recovered from cartilage tissue, namely from shark cartilage. The processes of obtention of cartilage extracts and the properties of the extracts themselves are disclosed in international publications WO 95/32722, WO 96/23512 and WO 97/16197. The processes generally comprise the steps of: homogenizing and extracting shark cartilage until a mixture of cartilage particles of an average size of about 500 $\mu$m and a crude liquid extract are obtained, separating said particles from said crude liquid extract, and fractionating said crude liquid extract so as to recover molecules having a molecular weight lower than about 500 KDa. These processes apply to the extraction of biological activities from any source of cartilage.

Shark cartilage liquid extracts have been tested in various assays and they comprise anti-angiogenic, anti-collagenolytic, direct anti-tumor proliferating and anti-inflammatory activities.

These cartilage extracts are described as being efficient against tumors and nevertheless innocuous since no serious adverse effect directly related to their oral administration has been observed in treated animals and human patients. The shark cartilage liquid extract and any other cartilage extract having equivalent anti-tumor activities are all within the scope of this invention and will be referred to as "cartilage extracts."

A large panel of therapeutic agents is known for treating cancer. Anti-neoplastics include, but are not limited to, those of the following TABLE 1:

| Alkylating Agents | |
| --- | --- |
| Alkyl Sulphonates | busulfan |
| Ethylene Imines | thiotepa |
| Nitrogen Mustard Analogues | chlorambucil |
| | cyclophosphamide |
| | estramustine sodium phosphate |
| | ifosfamide |
| | mechlorethamine hydrochloride |
| | melphalan |
| Nitrosoureas | carmustine |
| | lomustine |
| | streptozocin |
| Platinum-containing Compounds | carboplatin |
| | cisplatin |

| -continued | |
| --- | --- |
| Antimetabolites | |
| Folic Acid Analogues | methotrexate sodium |
| Purine Analogues | cladribine |
| | mercaptopurine |
| | thioguanine |
| Pyrimidine Analogues | cytarabine |
| | fluorouracil |
| Urea Derivatives | hydroxyurea |
| Cytotoxic Antibiotics | |
| Anthracyclines | daunorubicin |
| | doxorubicin hydrochloride |
| | epirubicin hydrochloride |
| | idarubicin hydrochloride |
| Actinomycins | dactinomycin |
| Various Cytotoxic Antibiotics | bleomycin sulfate |
| | mitomycin |
| | mitotane |
| | mitoxantrone hydrochloride |
| Plant Alkaloids and other Natural Products | |
| Epipodphyllotoxins | etoposide |
| | teniposide |
| Taxanes | docetaxel |
| | paclitaxel |
| Vinca Alkaloids and Analogues | vinblastine sulfate |
| | vincristine sulfate |
| | vindesine sulfate |
| | vinorelbine tartrate |
| Various Anti-neoplastics | |
| altretamine | |
| amsacrine | |
| I-asparaginase | |
| dacarbazine | |
| fludarabine phosphate | |
| porfimer sodium | |
| procarbazine hydrochloride | |
| tretinoin | |
| (all-trans retinoic acid), systemic | |
| Anti-angiogenics | Marimastat |
| | Suramin |
| | TNP 470 |
| | Thalidomide, and |
| Radiotherapeutics | |

Most of these anti-neoplastics or anti-tumor agents have a low safety margin since they are highly toxic, e.g. they provide severe undesirable effects at effective dosages.

It is an accepted fact, in the medical field, that no anti-tumor therapy is perfect. Pharmacologists and oncologists always have to deal with a compromise between a maximally effective dose and the toxic side effects thereof. As a result, an effective dose of a neoplastic may be given in a sub-maximal dose to avoid too severe toxic side effects to any possible extent. So, avoidance of severe toxic side effects unfortunately often has the priority of concern over maximal efficacy.

The cartilage extracts that we already described (op. cit.) are active in vivo against tumor proliferation, which activity appears to be due to a combination of at least a direct anti-tumor activity, anti-collagenolytic and anti-angiogenic activities. This extract has a well-proven anti-tumor activity and is devoid of toxic side effects. Since the current studies in the field aim at obtaining an anti-tumor therapy which would have close to 100% efficacy with close to 0% toxicity, it will be readily appreciated that anti-tumor compositions approaching these gold standards would be greatly welcome.

There is therefore a need for anti-neoplastic therapies combining high anti-tumor efficacy and low toxic side effects.

SUMMARY OF THE INVENTION

There is now provided improved anti-tumor therapies comprising administering an effective anti-tumor amount of an anti-neoplastic agent and an effective anti-tumor amount of a cartilage extract.

The overall advantageous contribution of the cartilage extract is addition to the efficacy of the anti-neoplastic and protection against toxic side effects.

It is therefore an object of the present invention to provide a use of a cartilage extract having anti-tumor activity in a combined anti-tumor therapy, to increase anti-tumor activity of an anti-neoplastic in a patient who is administered an anti-tumor amount of that anti-neoplastic and to protect the patient against an increase of toxic side effects inherent to the administration of the anti-neoplastic.

Combined anti-tumor therapy may take two forms: 1) administering to the patient a composition of an anti-neoplastic and a cartilage extract, and 2) administering to the patient an anti-neoplastic and a cartilage extract, separately, in a time-overlapping or simultaneous fashion (generally defined as "concurrent treatment").

In a specific embodiment, the cartilage extract is a shark cartilage extract obtained by a process comprising the steps of: homogenizing and extracting shark cartilage until a mixture of cartilage particles of an average size of about 500 $\mu$m and a crude liquid extract are obtained, separating said particles from said crude liquid extract, and fractionating said crude liquid extract so as to recover molecules having a molecular weight lower than about 500 KDa.

In a first preferred embodiment, the anti-tumor amount of the anti-neoplastic is a sub-optimal dose thereof, and the amount of cartilage extract given in combination adds anti-tumor efficacy to the anti-neoplastic with no increase, even better a decrease, of toxic side effects inherent to the administration of higher dose of the anti-neoplastic which would have an anti-tumor efficacy equivalent to the combined anti-tumor therapy.

In a second preferred embodiment, the anti-tumor amount of the anti-neoplastic is an optimal dose thereof, and the amount of cartilage extract given in combination adds anti-tumor efficacy to the anti-neoplastic with no increase, even better a decrease, of toxic side effects inherent to an administration of said anti-neoplastic.

The choice of a sub-optimal or optimal dose of an anti-neoplastic merely depends on the aggressivity sought for a treatment and the severity of the side effects of the anti-neoplastic.

The anti-neoplastic may be busulfan, thiotepa, chlorambucil, cyclophosphamide, estramustine sodium phosphate, ifosfamide, mechlorethamine hydrochloride, melphalan, carmustine, lomustine, streptozocin, carboplatin, cisplatin, methotrexate sodium, cladribine, mercaptopurine, thioguanine, cytarabine, fluorouracil, hydroxyurea, daunorubicin, doxorubicin hydrochloride, epirubicin hydrochloride, idarubicin hydrochloride, dactinomycin, bleomycin sulfate, mitomycin, mitotane, mitoxantrone hydrochloride, etoposide, teniposide, docetaxel, paclitaxel, vinblastine sulfate, vincristine sulfate, vindesine sulfate, vinorelbine tartrate, altretamine, amsacrine, I-asparaginase, dacarbazine, fludarabine phosphate, porfimer sodium, procarbazine hydrochloride, tretinoin (all-trans retinoic acid), marimastat, suramin, TNP 470, thalidomide or radiotherapy.

In a specific embodiment of the invention, the anti-neoplastic is cisplatin.

It is another object of this invention to provide products which may be used for bringing into practice the novel use for a cartilage extract.

One of the products is an anti-tumor composition comprising an anti-tumor amount of an anti-neoplastic and an anti-tumor amount of a cartilage extract, in a suitable pharmaceutically acceptable carrier.

Another one of these products is an anti-tumor treatment kit comprising a first component consisting of an anti-neoplastic in an anti-tumor dosage form and a second component consisting of a cartilage extract in an anti-tumor dosage form.

DESCRIPTION OF PREFERRED EMBODIMENTS OF THE INVENTION

We have tested combined anti-tumor therapies comprising administering a cartilage extract and an anti-neoplastic, hoping to find out if the efficacy of each other may be improved without any increase, or better with a decrease, of toxic side effects.

This invention will be described by way of preferred embodiments and with further reference to the following appended Figures, which purpose is to illustrate the invention rather than to limit its scope.

BRIEF DESCRIPTION OF FIGURES

FIG. 3 shows the correlation between the the white blood cell counts and the stringency of anti-tumor treatment with regard to toxicity.

RESULTS

Figure 1:
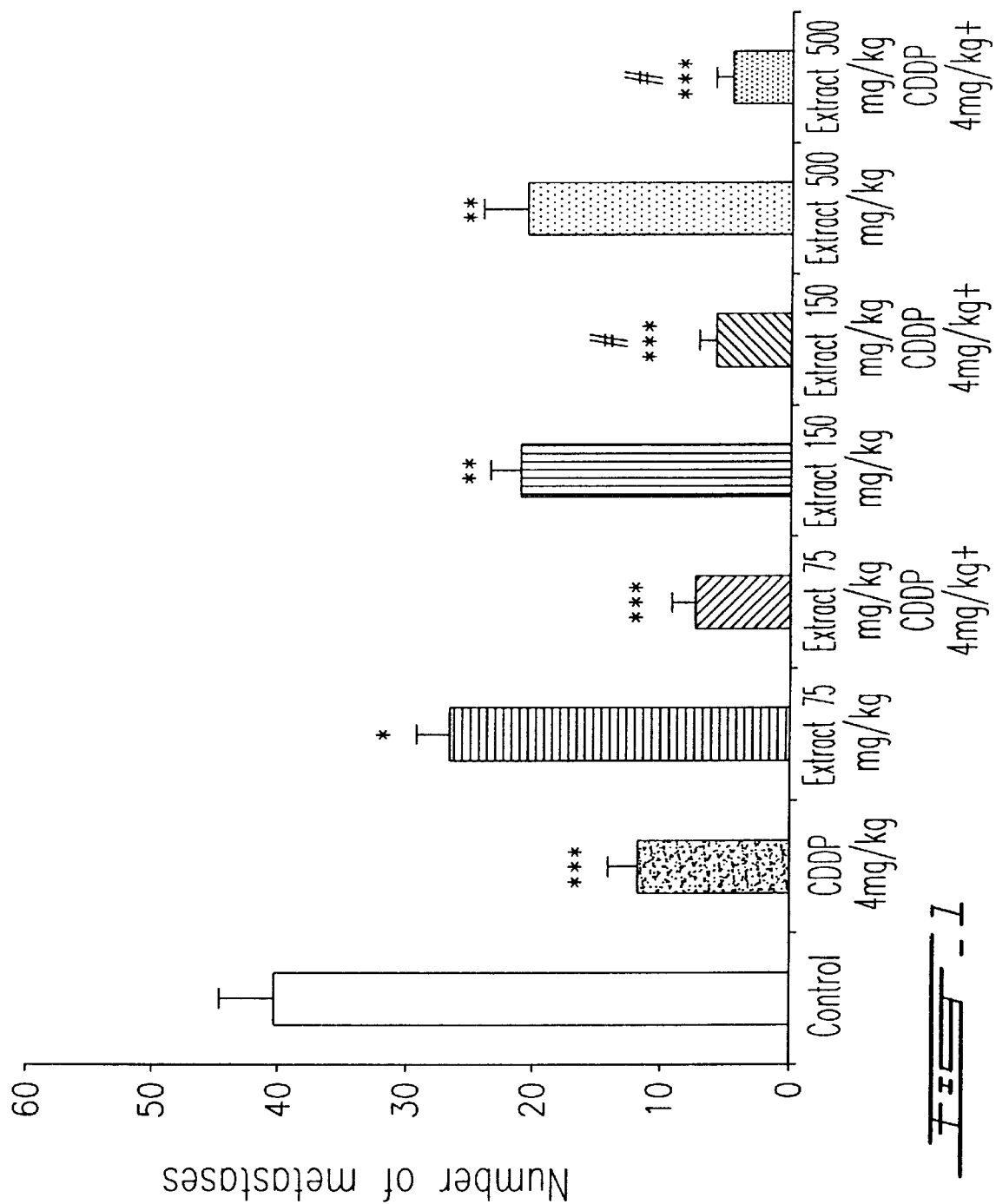
FIG. 1 shows the reduction in the number of metastases in LLC mouse tumor model. Increasing doses of cartilage liquid extract (AE-X) have been orally administered to LLC mice alone or in combination with cisplatin (CDDP). CDDP alone has also been tested alone. The control represents saline-treated mice.

We have characterized some ingredients from our proprietary shark cartilage liquid extract (op.cit.) and we have found the presence, amongst others, of hypoxanthine, its furanoside derivative, and dimers, in a total concentration of about 75 $\mu$g/20 mg of dry weight of total cartilage liquid extract. This amount of hypoxanthine should not be toxic in vivo although it is not excluded that it may be effective against tumors.

Hypoxanthine is a substrate for the enzyme hypoxanthine-guanine phosphoribosyl transferase (HGPRT), a purine salvaging enzyme (Weber et al.; 1983). Hypoxanthine forms inosine monophosphate, which is a key intermediate shared for production of adenylates and guanylates. Although hypoxanthine may ultimately lead to an increase of the incorporation of purine bases into nucleotides and nucleic acids, which would favorize DNA synthesis, many cellular systems make use of purines in various cellular pathways, some of which are activators while others are inhibitory. It is known that hypoxanthine has an in vitro anti-proliferative activity against tumor cells, which suggests that inhibitory pathways involving hypoxanthine may have precedence over activator ones in cancer cells.

In human subjects, anecdotal data show that the patients concurrently treated with the cartilage extract and radiotherapy or chemotherapy have recovered more rapidly and the general appearance and health of there nails and hair improve significantly. On the other hand, those patients taking only the cartilage extract have also seen their general health improving while cancer is regressing. These observations indicate that the cartilage extract is not only efficient by itself in tumor proliferation regression, but also that it counteracts and/or permits more rapid recovery from adverse effects of other anti-cancer therapies.

We have verified the in vivo anti-tumor activity of cartilage extract in two animal models:

DA3 mice, which tumors have a low metastatic potential; and

LLC mice, which tumors are highly metastatic.

DA3 model:

The anti-tumor potential of cartilage extract was studied in a mouse mammary adenocarcinoma model (allograft). DA3 cells ($1 \times 10^6$) were inoculated subcutaneously into the right flank of adult BALB/c mice. These cells originate from a murine mammary adenocarcinoma induced by 7,12-dimethylbenzanthracene (DMBA). DA3 is a non- or low-metastatic murine mammary carcinoma (D. Medina, J. Natl. Cancer Inst., 1969, 42: 303–310; ibid., 1976, 57: 1185–1189). Inoculated cells grow slowly in vivo and form a solid tumor with a low metastatic prognosis. DA3 cells were maintained in RPMI 1640 medium supplemented with 50 $\mu$M mercaptoethanol, 0.2 mM Hepes buffer solution, 1 mM Na-pyruvate, 2 mM L-glutamine, 0.1 mM non-essential amino acids, 10 mM vitamins, 10% fetal bovine serum and 1% penicillin streptomycin. The cells were incubated at 37° C. in atmosphere containing 5% $CO_2$. Under these conditions, DA3 cells proliferate but do not differentiate. For tumor induction, cells were grown to 70% confluence in complete medium and then collected using trypsin-EDTA solution Cells were centrifuged, washed three times with phosphate buffer solution (D-PBS, $Ca^{++}$ and $Mg^{++}$ free), and resuspended at a dilution of $1 \times 10^7$cells/ml. Mice (n=15) were inoculated with 0.1 ml of cell suspension and were given daily oral administration of cartilage extract or a placebo (saline solution). The treatments began the day of DA3 cell inoculation or 7 days later, after randomization of animals. Various concentrations of cartilage extract were tested. Cartilage extract dose levels are expressed as the amount of cartilage extract dry weight administered per kg of body weight.

Tumor growth was monitored every third day. Tumor length and width were measured and the relative tumor volume ($cm^3$) calculated as follows (Length (cm)×width$^2$ ($cm^2$)/2). Mice were sacrificed on the 54th days after tumor inoculation, at which time tumors were removed and weighed.

When doses of 100 to 400 mg/Kg of cartilage extract (dry weights) were daily administered to DA3 mice, a reduction of more 50% of tumor size after 48 days of treatment was observed (data not shown).

LLC Model:

We have verified the anti-tumor efficacy and the protective effect of cartilage extract by testing a combination of diverse concentrations of cartilage liquid extract alone and in combination with cisplatin (CDDP), in the Lewis lung carcinoma model (LLC).

LLC cells were resuspended in sterile PBS ($10^6$ cells/0.2 ml) and implanted in C57B1/6 mice. After a period of 11 days, primary tumors reached an average volume of 1.0 $cm^3$ and were surgically resected. After surgery, mice were randomized into groups of 15 animals and control article (saline) and cartilage extract were administered on a daily basis via oral gavage at the dose levels indicated for a period of 15 days. At day 16-post-surgery, animals were sacrificed, the lungs fixed in 10% formamide and the number of lung metastases counted. Animals were always kept under controlled environment: temperature 22° C., humidity 40% to 50%, light/dark cycle: 12 hours. They were fed and given to drink ad libitum.

In a first experiment, five injections of CDDP were given intraperitoneally every three days (1, 2 and 3 mg/Kg). Cartilage extract was given per os daily (31, 125 and 500 mg/Kg). Saline was given as a control. Results are summarized in Table 2.

TABLE 2

| CDDP | Percent reduction from control | | | |
|---|---|---|---|---|
| | Cartilage extract (mg/Kg) | | | |
| (mg/kg) | 0 | 31 | 125 | 500 |
| 3 | 54 | 60 | 69 | 85 |
| 2 | 35 | 46 | 69 | 73 |
| 1 | 19 | 39 | 69 | 65 |
| 0 | 0 | 23 | 65 | 69 |

It was observed that cartilage extract showed neither synergy nor antagonism but was additive in its ability to reduce LLC lung metastasis. CDDP alone at 3 mg/Kg provided 54% metastases reduction, while cartilage extract alone at 125 and 500 mg/Kg provided 65% and 69% reduction, respectively. The resulting decrease (85%) in metastases seen at the combination of the highest dose (500 mg/Kg/day) of cartilage extract and CDDP (3 mg) was equivalent to the one observed with CDDP alone at 5 mg/Kg, but without the toxicity observed at that higher dose of CDDP (data not shown). Thus, the addition of cartilage extract to a sub-optimal, low toxicity level dose of CDDP resulted in the maintenance of anti-metastatic activity usually observed at higher doses of CDDP.

In a second independent experiment, CDDP was given at a dose of 4 mg/Kg. Cartilage extract was given at doses 75, 150 and 500 mg/Kg. Saline was given again as a control. The results on the reduction of number of metastases are summarized in FIG. 1. Administration of CDDP alone reduced the number of metastases by about 71%.

Cartilage extract was effective in reducing the number of metastases at all tested doses. Maximal effect on metastase reduction occurs at the dose of 150 mg/Kg or higher.

The combination of the two highest doses of cartilage extract (150 and 500 mg/Kg) and CDDP provide a supra-maximal effect (85%–87%) when compared to the maximal effect observed with an optimal dose of CDDP alone (about 71%).

Figure 2:
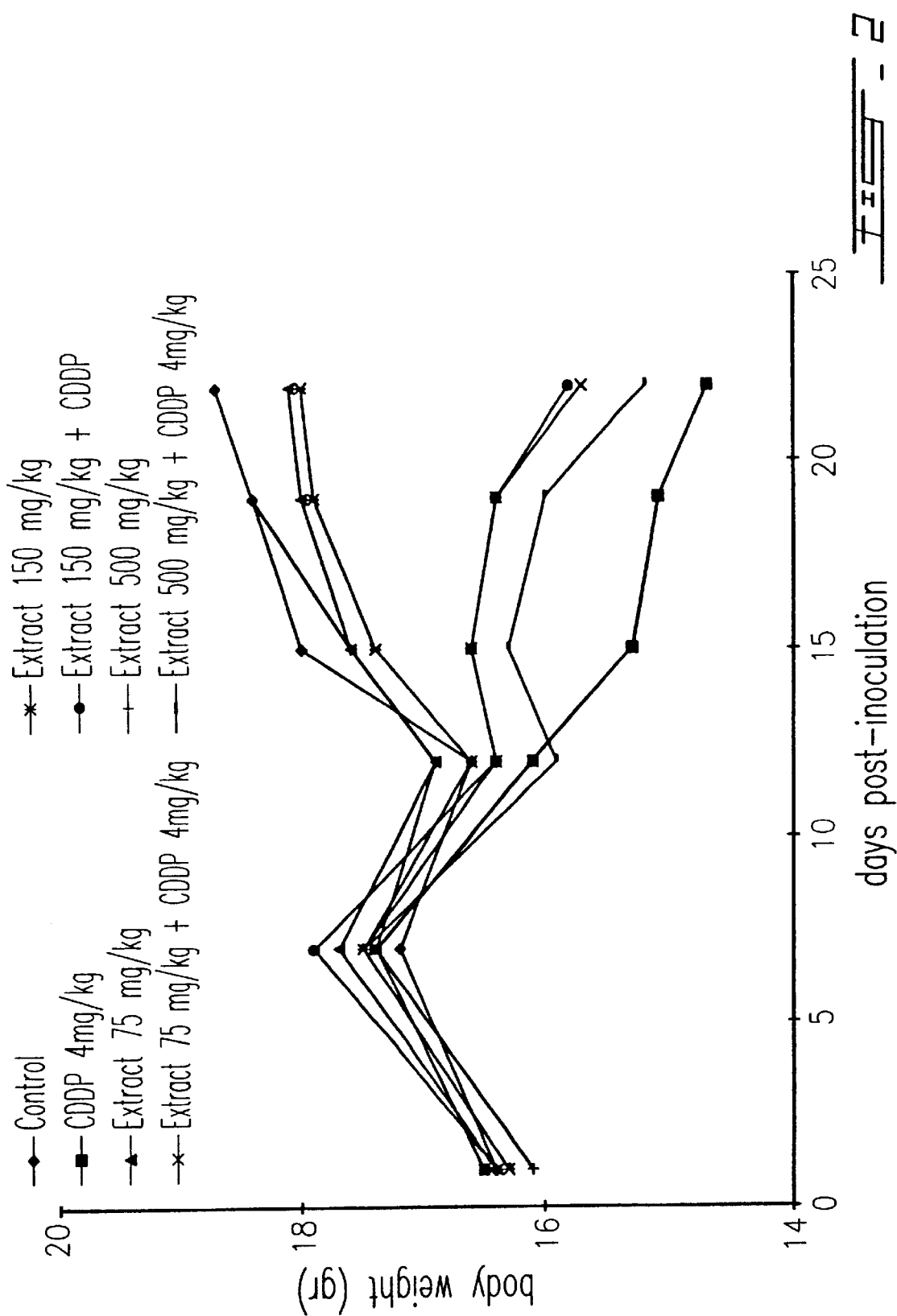
FIG. 2 shows the variations of body weights of LLC mice treated with cisplatin (CDDP), increasing amounts of cartilage liquid extract (AE-X), alone or in combination, compared with saline-treated animals (control).
Figure 7:
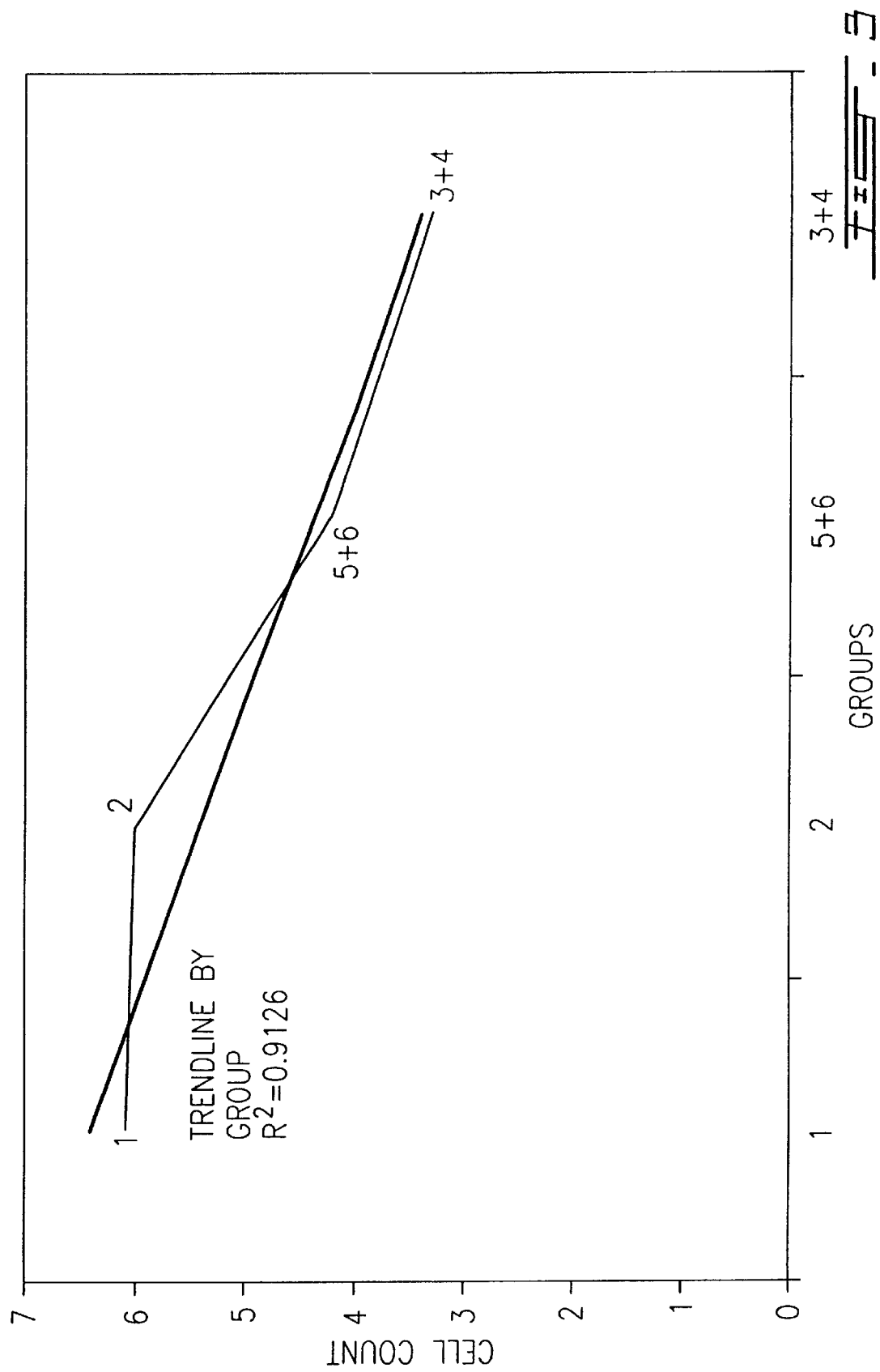

The toxic side effects were evaluated by measuring the body weights. The results are illustrated in FIG. 2.

During the first week of treatment, the body weights increased in all groups. Treatment started on Day 12 of the protocol. The decrease in body weight observed between the second and the third time point of the graph results from the surgery (on day 11) necessary to remove the primary LLC tumor mass. After fifteen days from inoculation, it was observed that CDDP alone was very toxic since a decrease of about 16% of body weight occurred in comparison to the non-treated group.

Cartilage extract alone, at all doses, did not affect the body weight decrease, while efficacious in the reduction of lung metastase numbers. When combined with CDDP, cartilage extract exerts a protective effect by reducing the loss of body weight triggered by CDDP (doses of 75, 150 and 500 mg/Kg cartilage liquid extract compared to CDDP; p<05 for the overall treatment period).

An overall dose of about 150–500 mg of cartilage extract can be combined to 3–4 mg CDDP to achieve supra-maximal effect with no increase of toxicity, even at the highest dose of CDDP.

Toxicity was evaluated in cancerous animals by the body weight decrease. We further characterized the nature of the protective effect provided by the cartilage extract by assessing an hematology parameter namely the number of peripheral white blood cells. Normal mice were injected (I.P.) with CDDP (3 and 4 mg/kg) on days 1, 4, 7, 10 and 13 of the experimental protocol. The cartilage extract was administered, orally, at doses of 75, 150 and 500 mg/kg/day. Animals were sacrificed on day 15 and blood samples were collected for cell count using an automated blood cell analyzer. Groups consisted of animals receiving CDDP alone, the cartilage extract alone, both in combination or saline as negative control.

Administration of CDDP resulted in a significant decrease of the number of white blood cells (Tables 3 and 4). Co-administration of the cartilage extract to CDDP protected against the reduction of the white blood cells (cartilage vs 3 mg/kg CDDP, $p<0.05$; cartilage vs 4 mg/kg CDDP, $p<0.01$). Values obtained from individual groups that have received cartilage extract were pooled to increase statistical power. Mean white blood cell counts were plotted according to treatment group regimen (FIG. 3). A linear trend indicated a clear monotonic trend ($r^2 = 0.9126$) for as decrease in cell counts according to treatment regimen stringency. This observation is in agreement with a protective effect of the cartilage extract relative to the peripheral white blood cell population reduced during CDDP administration.

TABLE 3

Number of white blood cells ($\times 10^9$/l)

| Group Number | #1 | #2 | #3 | #4 | #5 | #6 |
|---|---|---|---|---|---|---|
| Treatment | Control | Æ-X (75–500 mg/kg) | CDDP (3 mg/kg) | CDDP (4 mg/kg) | Æ-X (75–500 mg/kg) + CDDP (3 mg/kg) | Æ-X (75–500 mg/kg) + CDDP (4 mg/kg) |
| Number of white blood cells | 6.1 | 6.0 | 3.4 | 3.3 | 4.0 | 4.6 |
| N | 4 | 11 | 8 | 8 | 16 | 16 |

TABLE 4

Summary of contrasts of treatment

| Group Contrast | P-Value |
|---|---|
| gp 1 vs all others | 0.0045 |
| gp 3 vs gps 5 and 2 | 0.0233 |
| gp 4 vs gps 6 and 2 | 0.0015 |

Based on the biological activities demonstrated for the cartilage extract, it is now contemplated that cartilage extract may be used for complementing a large variety of anti-neoplastics. Combinations of known anti-neoplastics with cartilage extract will provide the great advantage of being highly efficacious and with no increase or even lower toxicity than an effective amount of the neoplastics used alone. We therefore provide a method for treating tumors, which comprises the steps of administering a combination of an anti-tumor amount of cartilage extract and an anti-tumor amount of an anti-neoplastic, whereby said combination provides for high efficacy and decreased side effects due to said anti-neoplastics. The anti-neoplastics are not limited to cisplatin. Indeed, those of Table 1 are all good candidate examples for the combinations of this invention.

The decreased toxic side effects comprises: hair and nail health improvement, diminution of nausea, gain of appetite and body weight, diminution of bone marrow depression, diminution of white blood cell counts decrease and a general diminution of morbidity and mortality.

This invention has been described hereinabove, with reference to specific embodiments. It is well within the ability of the skilled artisan to make modifications without departing from the above teachings. These modifications are within the scope of this invention as defined in the appended claims.

What is claimed:

1. A method of reducing the amount or severity of side effects caused by an anti-neoplastic agent during cancer or tumor therapy comprising the steps of:
   administering an anti-tumor amount of anti-neoplastic agent;
   administering a toxicity reducing amount of a shark cartilage extract sufficient to reduce the amount or severity of side effects caused by the anti-neoplastic agent; wherein said shark cartilage extract has been prepared according to a process comprising the step of:
   fractionating a crude cartilage extract comprising water soluble molecules obtained from shark cartilage material, wherein said fractionating removes molecules having a molecular weight of greater than about 500 kDa, thereby to form said shark cartilage extract.

2. The method of claim 1, wherein the anti-neoplastic agent is administered at an optimal dose and the shark cartilage extract enhances the efficacy of the anti-neoplastic agent and decreases the amount or severity of side effects caused by the anti-neoplastic agent.

3. The method of claim 1, herein the anti-neoplastic agent is administered at a sub-optimal dose and the shark cartilage extract enhances the efficacy of the anti-neoplastic agent to that of at least an optimal dose and decreases the amount or severity of side effects caused by the anti-neoplastic agent.

4. The method of claim 1, wherein the anti-neoplastic agent and the shark cartilage extract are administered concurrently or in a time-overlapping manner.

5. The method of claim 1, wherein the anti-neoplastic agent and the shark cartilage extract are administered sequentially.

6. The method of claim 1, wherein the anti-neoplastic agent is selected from the group consisting of busulfan, thiotepa, chlorambucil, cyclophosphamide, estramustine sodium phosphate, ifosfamide, mechlorethamine hydrochloride, melphalan, carmustine, lomustine, streptozocin, carboplatin, cisplatin, methotrexate sodium, cladribine, mercaptopurine, thioguanine, cytarabine, fluorouracil, hydroxyurea, daunorubicin, doxorubicin hydrochloride, epirubicin hydrochloride, idarubicin hydrochloride, dactinomycin, bleomycin sulfate, mitomycin, mitotane, mitoxantrone hydrochloride, etoposide, teniposide, docetaxel, paclitaxel, vinblastine sulfate, vincristine sulfate, vindesine sulfate, vinorelbine tartrate, altretamine, amsacrine, l-asparaginase, dacarbazine, fludarabine phosphate, porfimer sodium, procarbazine hydrochloride, tretinoin (all-trans retinoic acid), marimastat, suramin, TNP 470, thalidomide and radiotherapy and combinations thereof.

7. The method of claim 1, wherein the shark cartilage extract protects against the reduction of white blood cells caused by the anti-neoplastic agent.

8. The method of claim 1, wherein the shark cartilage extract protects against excessive weight loss caused by the anti-neoplastic agent.

9. The method of claim 1, wherein the cancer or tumor therapy is carcinoma therapy.

10. The method of claim 9, wherein the carcinoma therapy is lung carcinoma therapy.

11. The method of claim 1, wherein the shark cartilage extract provides a decrease in morbidity or mortality in a first population as compared to the morbidity or mortality achieved by a similar second population not being administered the shark cartilage extract.

12. The method of claim 1, wherein the shark cartilage extract at least one of:

protects against excessive hair loss caused by the anti-neoplastic agent;

reduces the incidence of nausea typically associated with administration of the anti-neoplastic agent;

improves nail and hair health in a first population as compared to that achieved by a similar second population not being administered the shark cartilage extract; and reduces the incidence of bone marrow suppression typically associated with administration of the anti-neoplastic agent.

13. The method of claim 1, wherein the process for preparing the shark cartilage extract further comprises the step of separating shark cartilage particles from a liquid to form the crude liquid extract.

14. The method of claim 13, wherein the process for preparing the shark cartilage extract further comprises the step of reducing the particle size of a shark cartilage material and extracting molecules having a molecular weight lower than about 500 kDa from the shark cartilage material.

15. The method of claim 14, wherein the step of reducing the particle size comprises homogenizing shark cartilage material in a liquid to form particles having an average particle size of about 500 $\mu$ 16. The method of claim 15, wherein the homogenizing step is conducted in an aqueous-solution.

* * * * *

UNITED STATES PATENT AND TRADEMARK OFFICE
CERTIFICATE OF CORRECTION

PATENT NO.      : 6,383,522 B1
DATED           : May 7, 2002
INVENTOR(S)     : Eric Dupont It is certified that error appears in the above-identified patent and that said Letters Patent is hereby corrected as shown below:

<u>Column 8,</u>
Line 41, change "herein" to -- wherein --.

Signed and Sealed this

Sixth Day of August, 2002

Attest:

Attesting Officer

JAMES E. ROGAN
*Director of the United States Patent and Trademark Office*